United States Patent [19]

Ishimura et al.

[11] Patent Number: 5,001,246
[45] Date of Patent: Mar. 19, 1991

[54] PROCESS FOR PREPARATION OF AMINOPROPYLALKOXYSILANE

[75] Inventors: Yoshimasa Ishimura; Nobuyuki Nagato; Hideo Takahashi, all of Kawasaki, Japan

[73] Assignee: Showa Denko K.K., Tokyo, Japan

[21] Appl. No.: 477,385

[22] Filed: Feb. 9, 1990

[30] Foreign Application Priority Data

Feb. 10, 1989 [JP] Japan .................................. 1-32166

[51] Int. Cl.$^5$ ............................ C07F 7/10; C07F 7/18
[52] U.S. Cl. .................................... 556/413; 556/424
[58] Field of Search ............................... 556/413, 424

[56] References Cited

U.S. PATENT DOCUMENTS

| | | | |
|---|---|---|---|
| 4,556,722 | 12/1985 | Quirk et al. | 556/413 |
| 4,888,436 | 12/1989 | Shiozawa et al. | 556/413 |
| 4,897,501 | 1/1990 | Takatsuma et al. | 556/413 |
| 4,921,988 | 5/1990 | Takatsuma et al. | 556/413 |
| 4,927,949 | 5/1990 | Kobeta et al. | 556/413 |

Primary Examiner—Paul F. Shaver
Attorney, Agent, or Firm—Sughrue, Mion, Zinn, Macpeak & Seas

[57] ABSTRACT

A process for the preparation of an aminopropylalkoxysilane, which comprises reacting a hydrosilane compound with an allylamine compound in the presence of at least one member selected from the group consisting of phosphorus compounds having a phosphorus-nitrogen bond, which are represented by the following formulae:

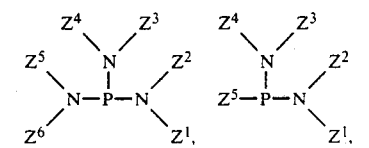

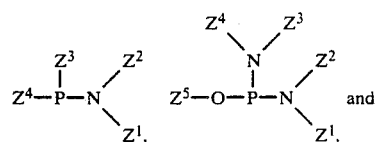

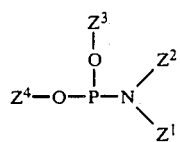

wherein $Z^1$, $Z^2$, $Z^3$, $Z^4$, $Z^5$ and $Z^6$ independently represent a hydrogen atom, an aliphatic hydrocarbon group having 1 to 8 carbon atoms, an alicyclic hydrocarbon group having 5 to 8 carbon atoms or an aromatic hydrocarbon group, and a rhodium compound.

According to this process, the aminopropylalkoxysilane can be prepared in a high yield at a low cost and a high efficiency, while controlling the formation of the $\beta$-compound to a very low level.

19 Claims, No Drawings

PROCESS FOR PREPARATION OF AMINOPROPYLALKOXYSILANE

BACKGROUND OF THE INVENTION

1. Field of the Invention

The present invention relates to a process for preparing an aminopropylalkoxysilane from a hydrosilane compound and an allylamine compound. More particularly, the present invention relates to a process for the preparation of an aminopropylalkoxysilane in which the reaction is carried out in the presence of a phosphorus compound having a phosphorus-nitrogen bond and a rhodium compound.

2. Description of the Related Art

The present invention relates to a process for preparing an aminopropylalkoxysilane, to improve the adhesive force between an inorganic filler or substrate and an organic resin, for example, between a glass and a a plastic material.

A γ-aminopropyltrialkoxysilane is conventionally prepared by adding a trialkoxysilane to acrylonitrile and hydrogenating the nitrile group to form an amine, but according to this process, the yield in the hydrogenation of the nitrile is low, and therefore, the product is expensive.

An aminopropyltrialkoxysilane also can be synthesized by adding a trialkoxysilane to allylamine, and since the reaction is a one-stage reaction, the aminopropyltrialkoxysilane can be prepared at a low cost. Nevertheless, the reaction between allylamine and a trialkoxysilane, forms a β-aminopropyltrialkoxysilane as a by-product, although only a γ-compound is formed if the synthesis reaction is carried out between acrylonitrile and a trialkoxysilane.

Since the object of the present invention is to obtain an aminopropylalkoxysilane which is a γ-compound, it is necessary to control the formation of the β-compound as the by-product to as low a level as possible. A platinum type catalyst is known as the catalyst for the reaction between allylamine and hydrosilane, but if the platinum type catalyst is used, not only the desired γ-compound but also 6% of the β-compound as the by-product is formed by the addition reaction (see the specification of U.S. Pat. No. 4,481,364). As the means for controlling the formation of the β-compound as the by-product, a method has been proposed of using a rhodium-triorganic phosphorus complex catalyst (see U.S. Pat. No. 4,556,722). The triorganic phosphorus is defined as a compound in which each organic residue is bonded by a single valency to the phosphorus atom through a carbon atom or an oxygen atom of an aliphatic ether.

According to this known method, the formation of the β-compound as the by-product can be controlled, but the control effect is still too low. Further, a large quantity of the triorganic phosphorus compound as the catalyst must be used.

A method is also known in which, by using a rhodium-carbonyl complex as the catalyst, the reaction between allylamine and hydrosilane is promoted while controlling the formation of the β-compound as the by-product (see Japanese Unexamined Patent Publication No. 64-89).

In this method, the β-compound is still formed in an amount of 5 to 6%, and thus a further improvement is desired. The valency of the rhodium metal in the rhodium-carbonyl complex is 0 or negative, and an organic group sucn as triphenylphosphine is not contained as the ligand.

SUMMARY OF THE INVENTION

The inventors carried out research with a view to solving the above-mentioned problems of the conventional techniques, and as a result, found that, by using a rhodium compound and at least one phosphorus compound having a phosphorus-nitrogen bond as the catalyst for the reaction between a hydrosilane compound and an allylamine compound, a γ-compound of an aminopropylalkoxysilane can be selectively prepared at a γ-compound purity of, for example, at least 98.5% while using an industrially applicable amount of the catalyst. The present invention is based on this finding.

More specifically, in accordance with the present invention, there is provided a process for the preparation of an aminopropylalkoxysilane, which comprises reacting a hydrosilane compound with an allylamine compound in the presence of at least one member selected from the group consisting of phosphorus compounds having a phosphorus-nitrogen bond, which are represented by the following formulae:

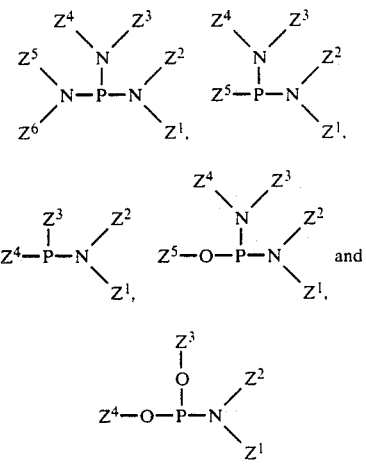

wherein $Z^1$, $Z^2$, $Z^3$, $Z^4$, $Z^5$, and $Z^6$ independently represent a hydrogen atom, an aliphatic hydrocarbon group having 1 to 8 carbon atoms, an alicyclic hydrocarbon group having 5 to 8 carbon atoms, or an aromatic hydrocarbon group, and a rhodium compound.

DESCRIPTION OF THE PREFERRED EMBODIMENTS

The hydrosilane compound referred to in the present invention is a silane compound represented by the following general formula:

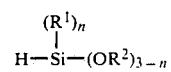

wherein $R^1$ represents a hydrogen atom, an aliphatic hydrocarbon group having 1 to 8 carbon atoms or an aromatic hydrocarbon group, $R^2$ represents a lower alkyl group, and n is 0, 1 or 2. As the hydrosilane compound used in the present invention, there can be mentioned trimethoxysilane, triethoxysilane, tripropoxysilane, triisopropoxysilane, tributoxysilane, triisobutoxysilane, methyldimethoxysilane, methyldiethoxysilane, methyldipropoxysilane, methyldibutoxysilane, ethyldimethoxysilane, ethyldiethoxysilane, vinyldimethoxysilane, vinyldiethoxysilane, phenyldimethoxysilane, phenyldiethoxysilane, dimethylmethoxysilane, and dimethylethoxysilane. Note, the hydrosilanes that can be used in the present invention are not limited to those exemplified above.

The amine compound referred to in the present invention is an amine compound represented by the following general formula:

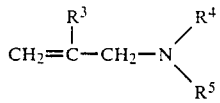

Wherein $R^3$ represents a hydrogen atom or a lower alkyl group, and $R^4$ and $R^5$ independently represent a hydrogen atom, a lower alkyl group or a lower alkyl group substituted by a substituent containing at least one nitrogen atom.

As the allylamine used in the present invention, there can be mentioned monoallylamine, diallylamine, triallylamine, methallylamine, N-methylallylamine, N,N-dimethylallylamine, N-ethylallylamine, N,N-diethylallylamine, N-allylaniline, N,N-methylallylaniline, allylethylenediamine, allyldiethylenetriamine, and N,N-dimethyl-N'-allylethylenediamine. Note, the allylamines that can be used in the present invention are not limited to those exemplified above.

In the rhodium compound used as the catalyst in the present invention, the rhodium metal (Rh) has a valency of from +1 to +3.

As examples of the compound wherein the valency of Rh is +1, there can be mentioned.

$RhCl[P(C_6H_5)_3]_3$,
$[RhCl(CO)_2]_2$,
$RhCl(C_8H_{14})_2$,
$RhCl(t-BuNc)_4$,
$[RhCl(C_2H_4)]_2$, and
$RhCl(CO)[P(C_6H_5)_3]_2$.

As examples of the compound wherein the valency of Rh is +2, there can be mentioned
$[Rh(OCOCH_3)_2]_2$, and
$[Rh(OCOCF_3)_2]_2$.

As examples of the compound wherein the valency of Rh is +3, there can be mentioned
$RhCl_3$, and
$Rh(CH_2COCH_2COCH_3)_3$.

The present invention is characterized in that a phosphorus compound having a phosphorus-nitrogen bond is made present together with the above-mentioned rhodium compound. Namely, a P-N bond must be contained in the phosphorus compound used in the present invention. More specifically, at least one member selected from the group consisting of phosphorus compounds having a phosphorus-nitrogen bond, which are represented by the following formulae, is used:

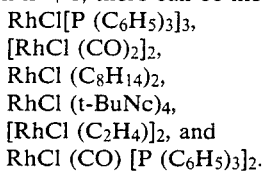

wherein $Z^1$, $Z^2$, $Z^3$, $Z^4$, $Z^5$ and $Z^6$ independently represent a hydrogen atom, an aliphatic hydrocarbon group having 1 to 8 carbon atoms, an alicyclic hydrocarbon group having 5 to 8 carbon atoms, or an aromatic hydrocarbon group.

As examples of the phosphorus compound used in the present invention, there can be mentioned.

$P[N(CH_3)_2]_3$,
$P[N(C_2H_5)_2]_3$,
$P[N(n-C_3H_7)_2]_3$,
$P[N(iso-C_3H_7)_2]_3$,
$P[N(n-C_4H_9)_2]_3$,
$P[N(iso-C_4H_9)_2]_3$,
$P[N(t-C_4H_9)_2]_3$,
$P[N(CH_3)_2]_2[N(C_2H_5)_2]$,
$P[N(CH_3)_2][N(C_2H_5)_2]_2$,
$P[N(CH_3)(C_6H_5)]_3$,
$P[N(CH_3)(cyclo-C_6H_{11})]_3$,
$P[N(C_3H_5)_2]_3$,
$P[N(CH_3)_2]_2[N(CH_3)(C_6H_5)]$,
$P(C_6H_5)_2[N(n-C_4H_9)_2]$,
$P(C_2H_5)_2[N(CH_3)_2]$,
$P(C_6H_5)[N(n-C_4H_9)_2]_2$,
$P(n-C_4H_9)_2[N(n-C_4H_9)_2]$,
$P(OC_2H_5)_2[N(n-C_4H_9)_2]$,
$P(OCH_3)[N(CH_3)_2]_2$,
$P(OC_6H_5)_2[N(C_2H_5)_2]$, and
$P(C_6H_5)_2[N(CH_3)(C_6H_5)]$.

Note, the phosphorus compounds that can be used in the present invention are not limited to those exemplified above.

The reaction of the present invention is advantageously advanced if hydrogen is present together with the rhodium compound and the phosphorus compound having a phosphorus-nitrogen bond. The amount of hydrogen gas present is 1/1000 to 10 kg/cm², preferably 1/10 to 3 kg/cm², expressed as the hydrogen pressure under normal temperature.

The reaction of the present invention is even more advantageously advanced if a carboxylic acid is present in the reaction system.

As the carboxylic acid to be used in the present invention, there can be mentioned benzoic acid, phthalic acid, isophthalic acid, terephthalic acid, maleic acid, phthalic anhydride, cyclohexanecarboxylic acid, and acetic acid. Note, the carboxylic acids that can be used in the present invention are not limited to those exemplified above.

In the process of the present invention, the catalyst comprising a rhodium compound and a phosphorus compound having at least one phosphorus-nitrogen bond in combination, as described above, is preferably used in an amount of 1/10 to 1/100,000 mole, especially 1/50 to 1/20,000 mole, per mole of the hydrosilane compound. The phosphorus compound can be used in an amount such that the molar ratio to the rhodium metal of the rhodium compound is from 1 to 20, and even if the phosphorus compound is used in an excessive amount such that the above-mentioned molar ratio is from 20 to 100, no particular problem arises. Where a phosphorus compound having at least one phosphorus-nitrogen bond is contained in the rhodium compound, a phosphorus compound having at least one phosphorus-nitrogen bond need not be particularly added. In the present invention, the use of a phosphorus compound having at least one phosphorus-nitrogen bond is indispensable, but the presence of a triorganic phosphorus compound such as a triarylphosphine, a trialkylphosphine, a triaryl phosphite or a trialkyl phosphite is permissible.

In the process of the present invention, the allylamine compound is preferably used in an amount such that the molar ratio to the hydrosilane compound is from 1/100 to 100, especially from 1/10 to 10. The reaction between the hydrosilane compound and allylamine compound is carried out at a temperature of 0° to 200° C., preferably 30° to 170° C.

In the process of the present invention, the reaction can be carried out in the presence or absence of a solvent. As examples of the solvent used in the present invention, there can be mentioned benzene, toluene, xylene, diethylene glycol dimethyl ether, triethylene glycol dimethyl ether, tetraethylene glycol dimethyl ether, dioxane, and silicone oil.

The present invention will now be described in detail with reference to the following examples, that by no means limit the scope of the invention.

EXAMPLE 1

A 50 cc stainless steel microautoclave provided with a magnetic stirrer was charged with 0.01 g of $[Rh(OCOCH_3)_2]_2$, 5 g of benzene and 0.1 g of $P[N(CH_3)(cyclo-C_6H_{11})]_3$, and 8.62 g of triethoxysilane and 2.85 g of monoallylamine were added thereto. A reaction was then carried out at 100° C., while stirring, for 2 hours.

The product obtained was 8.7 g of γ-aminopropyltriethoxysilane, the selectivity to γ-aminopropyltriethoxysilane based on monoallylamine was 87%, and the amount of β-aminopropyltriethoxysilane formed as the by-product was 0.09 g. This amount corresponded to 1.03% based on the aminopropyltriethoxysilane.

Note, the confirmation and determination of the products were carried out by gas chromatography (GC), NMR, GC-MS, and the like.

EXAMPLES 2 THROUGH 14

The reaction was carried out in the same manner as described in Example 1 except that the conditions were changed as shown in Table 1. The results are shown in Table 1.

TABLE 1

| Example No. | Rh Compound (g) | Phosphorus Compound (g) | Solvent (g) | Alkoxysilane (g) | Monoallylamine (g) | Yield of γ-Aminopropyl-alkoxysilane (%) | Selectivity to γ-Compound (%) | β/(β + γ) × 100 (%) |
|---|---|---|---|---|---|---|---|---|
| 2 | $[Rh(OCOCH_3)_2]_2$ 0.01 | $P[N(CH_3)(cyclo-C_6H_{11})]_3$ 0.01 | benzene 5 | triethoxysilane 8.62 | 2.85 | 7.73 | 77.02 | 1.04 |
| 3 | $[Rh(OCOCH_3)_2]_2$ 0.005 | $P[N(CH_3)(cyclo-C_6H_{11})]_3$ 0.005 | benzene 5 | triethoxysilane 8.62 | 2.85 | 8.67 | 81.72 | 1.07 |
| 4 | $[Rh(OCOCH_3)_2]_2$ 0.01 | $P[N(C_3H_5)_2]_3$ 0.04 | benzene 5 | triethoxysilane 8.62 | 2.85 | 8.35 | 82.27 | 1.30 |
| 5 | $[Rh(OCOCH_3)_2]_2$ 0.01 | $P[N(CH_3)_2]_3$ 0.01 | benzene 5 | triethoxysilane 8.62 | 2.85 | 9.26 | 86.67 | 1.47 |
| 6 | $[Rh(OCOCH_3)_2]_2$ 0.005 | $P[N(CH_3)(cyclo-C_6H_{11})]_3$ 0.05 | — | triethoxysilane 8.62 | 2.85 | 9.15 | 85.33 | 1.25 |
| 7 | $[Rh(OCOCH_3)_2]_2$ 0.01 | $P[N(CH_3)(cyclo-C_6H_{11})]_3$ 0.08 | Silicone Oil KF-54 10 | triethoxysilane 18.04 | 5.70 | 17.10 | 82.03 | 1.19 |
| 8 | $[Rh(OCOCH_3)_2]_2$ 0.01 | $P[N(CH_3)(cyclo-C_6H_{11})]_3$ 0.08 | tetraethylene glycol dimethyl ether 5 | triethoxysilane 9.02 | 2.85 | 7.96 | 76.61 | 1.22 |
| 9 | $[RhCl(CO)_2]_2$ 0.01 | $P[N(CH_3)_2]_3$ 0.01 | benzene 5 | triethoxysilane 8.62 | 2.85 | 8.30 | 78.84 | 1.42 |
| 10 | $[RhCl(CO)_2]_2$ 0.01 | $P[N(C_2H_5)_2][N(CH_3)_2]_2$ 0.01 | benzene 5 | trimethoxysilane 6.97 | 2.85 | 6.69 | 77.7 | 1.11 |
| 11 | $[RhCl(CO)_2]_2$ 0.01 | $P[N(C_2H_5)_2][N(CH_3)_2]_2$ 0.02 | benzene 5 | trimethoxysilane 6.97 | 2.85 | 7.76 | 87.2 | 1.28 |
| 12 | $[RhCl(CO)_2]_2$ 0.01 | $P[N(C_3H_5)_2]_3$ 0.01 | benzene 5 | triethoxysilane 8.62 | 2.85 | 8.44 | 77.6 | 1.49 |
| 13 | $[RhCl(CO)_2]_2$ 0.02 | $P[N(C_3H_5)_2]_3$ 0.02 | benzene 10 | triethoxysilane 17.24 | 5.70 | 17.50 | 81.0 | 1.39 |
| 14 | $[RhCl(CO)_2]_2$ 0.01 | $P[N(CH_3)_2]_3$ 0.01 | benzene 5 | trimethoxysilane | 2.85 | 7.73 | 89.3 | 1.21 |

TABLE 1-continued

| Example No. | Rh Compound (g) | Phosphorus Compound (g) | Solvent (g) | Alkoxy-silane (g) | Mono-allyl-amine (g) | Yield of γ-Aminopropyl-alkoxysilane (%) | Selectivity to γ-Compound (%) | β/(β + γ) × 100 (%) |
|---|---|---|---|---|---|---|---|---|
| | | | | | 6.97 | | | |

Note
In each example, the reaction was carried out at 100° C. for 2 hours.

EXAMPLE 15

A 100 cc microautoclave provided with a magnetic stirrer was charged with 0.002 g of [Rh(OCOCH$_3$)$_2$]$_2$, 5 g of benzene and 0.027 g (0.09 millimole) of P(C$_6$H$_5$)$_2$[N(n-C$_4$H$_9$)$_2$], and 18.70 g of triethoxysilane and 5.70 g of monoallylamine were added thereto. The microautoclave was plugged and hydrogen gas was introduced therein to a gauge pressure of 2 kg/cm$^2$. A reaction was then carried out at 150° C. for 3 hours.

The product obtained was 13.29 g of γ-aminopropyltriethoxysilane, and the amount of the β-compound formed as the by-product was 0.2 g, which corresponded to 1.48% based on the aminopropyltriethoxysilane.

EXAMPLE 16

A 100 cc stainless steel microautoclave provided with a magnetic stirrer was charged with 0.01 g of [Rh(OCOCH$_3$)$_2$]$_2$ and 0.1 g of P(OC$_2$H$_5$)$_2$[N(n—C$_4$H$_9$)$_2$], and 18.70 g of triethoxysilane and 5.70 g of monoallylamine were added thereto. A reaction was then carried out at 100° C. for 2 hours, while stirring.

The product obtained was 16.90 g of γ-aminopropyltriethoxysilane, and 0.21 g of the β-compound was formed as the by-product, and this amount corresponded to 1.23% based on the aminopropyltriethoxysilane.

EXAMPLE 17

A 50 cc stainless steel microautoclave provided with a magnetic stirrer was charged with 0.01 g of [Rh(OCOCH$_3$)$_2$]$_2$ and 0.1 g of P[N(CH$_3$)(cyclo-C$_6$H$_{11}$)]$_3$, and 8.62 g of triethoxysilane and 6.40 g of CH$_2$=CH—CH$_2$—NH—CH$_2$—CH$_2$—N(CH$_3$)$_2$ were added thereto. A reaction was then carried out at 100° C. for 3 hours, while stirring.

The product obtained was 8.54 g of γ-(C$_2$H$_5$O)$_3$Si—CH$_2$—CH$_2$—CH$_2$—NH—CH$_2$—CH$_2$—N —(CH$_3$)$_2$, and 0.12 g of the β-compound was formed as the by-product.

EXAMPLE 18

A 100 cc stainless steel microautoclave provided with a magnetic stirrer was charged with 0.0005 g of [Rh(OCOCH$_3$)$_2$]$_2$, 5 g of benzene, 0.018 g of P(C$_6$H$_5$)$_2$[N(n—C$_4$H$_9$)$_2$] and 0.40 g of benzoic acid, and 16.94 g of triethoxysilane and 6.39 g of monoallylamine were added thereto. The microautoclave was plugged and hydrogen gas was introduced therein to a gauge pressure of 2 kg/cm$^2$. A reaction was then carried out at 150° C. for 6 hours, while stirring.

The product obtained was 11.57 g of γ-aminopropyltriethoxysilane. The amount of the β-compound formed as the by-product was 0.16 g, which corresponded to 1.36% based on the aminopropyltriethoxysilane.

EXAMPLES 19 THROUGH 25

The reaction was carried out in the same manner as described in Example 18 except that a carboxylic acid shown in Table 2 was made present. The conditions and results are shown in Table 2.

TABLE 2

| Example No. | Carboxylic Acid (g) | Triethoxysilane (g) | Monoallylamine (g) | Amount (g) of Obtained γ-Aminopropyltriethoxysilane (g) | β/(β + γ) · 100 (%) |
|---|---|---|---|---|---|
| 19 | phthalic acid 0.20 | 17.02 | 6.26 | 10.88 | 1.36 |
| 20 | isophthalic acid 0.20 | 17.00 | 6.35 | 12.83 | 1.48 |
| 21 | terephthalic acid 0.20 | 17.02 | 6.24 | 11.77 | 1.33 |
| 22 | maleic acid 0.20 | 17.00 | 6.20 | 9.50 | 1.40 |
| 23 | phthalic acid 0.20 | 17.05 | 6.25 | 10.87 | 1.22 |
| 24 | cyclohexane-carboxylic acid 0.20 | 16.90 | 6.20 | 10.76 | 1.40 |
| 25 | acetic acid 0.20 | 17.57 | 6.28 | 13.03 | 1.05 |

Note
Rh compound: [Rh(OCOCH$_3$)$_2$]$_2$, 0.0005 g
Phosphorus compound: P(C$_6$H$_5$)$_2$[N(n-C$_4$H$_9$)$_2$], 0.018 g
Solvent: benzene, 5 ml
Hydrogen pressure: 2 kg/cm$^2$ (normal temperature)
Apparatus: 100 ml stainless steel microautoclave
Reaction temperature: 150° C.
Reaction time: 6 hours

EXAMPLE 26

A 100 cc stainless steel microautoclave equipped with a magnetic stirrer was charged with 0.0005 g of [Rh(OCOCH$_3$)$_2$]$_2$ and 0.012 g of P(C$_6$H$_5$)$_2$[N(n-C$_4$H$_9$)$_2$], and 18.72 g of triethoxysilane and 6.39 g of monoallylamine were added thereto, and a reaction was carried out at 150° C. for 6 hours, while stirring. The product obtained was 6.26 g of γ-aminopropyltriethoxysilane, and the amount of the β-compound formed as the by-product was 0.08 g, which corresponded to 1.40% based on the aminopropyltriethoxysilane.

EXAMPLE 27

A 100 cc stainless steel microclave equipped with a magnetic stirrer was charged with 0.0005 g of [Rh(OCOCH$_3$)$_2$]$_2$ and 0.012 g of P(C$_6$H$_5$)$_2$[N(n-C$_4$H$_9$)$_2$], and 18.82 g of triethoxysilane and 6.27 g of monoallylamine were added thereto. The microautoclave was plugged and hydrogen gas was introduced therein to a gauge pressure of 2 kg/cm$^2$.

A reaction was then carried out at 150° C. for 6 hours, while stirring. The product obtained was 8.07 g of γ-aminopropyltriethoxysilane, and the amount of the β-compound formed as the by-product was 0.11 g, which corresponded to 1.34% of the aminopropyltriethoxysilane.

The reaction of the present invention is advantageously advanced if hydrogen is present together with the rhodium compound and the phosphorus compound having a phosphorus-nitrogen compound. For example, the yield of γ-aminopropyltriethoxysilane in Example 27, where hydrogen was made present, was more than 40% that of the yield obtained in Example 26 where hydrogen was not made present.

The amount of hydrogen gas present in the reaction system is 1/1000 to 10 kg/cm$^2$, preferably 1/10 to 3 kg/cm$^2$, expressed as the hydrogen pressure at normal temperature.

Furthermore, the reaction of the present invention is advantageously carried out if a carboxylic acid is made present. As seen from Example 18 and Table 2, if a carboxylic acid was made present, the yield was more than 70 to 130% that of the yield obtained in Example 26 wherein a carboxylic acid was not present.

As the carboxylic acid to be used for the reaction of the present invention, there can be mentioned benzoic acid, phthalic acid, isophthalic acid, terephthalic acid, maleic acid, phthalic anhydride, cyclohexanecarboxylic acid, and acetic acid. Note, the carboxylic acids that can be used are not limited to those exemplified.

EXAMPLE 28

A 100 cc stainless steel microautoclave equipped with a magnetic stirrer was charged with 0.0006 g of RhCl$_3$.3H$_2$O, 5 g of benzene, 0.002 g of P(C$_6$H$_5$)$_2$[N(n—C$_4$H$_9$)$_2$] and 0.4 g of benzoic acid, and 16.94 g of triethoxysilane and 6.2 g of monoallylamine were added thereto. The microautoclave was plugged and hydrogen gas was introduced therein to a gauge pressure of 2 kg/cm$^2$.

A reaction was then carried out at 150° C. for 6 hours, while stirring.

The product obtained was 8.37 g of γ-aminopropltriethoxysilane, and the amount of the β-compound formed as the by-product was 0.13 g, which corresponded to 1.53% based on the aminopropyltriethoxysilane.

COMPARATIVE EXAMPLE A 100 cc stainless steel microautoclave equipped with a magnetic stirrer was charged with 0.002 g of [Rh(OCOCH$_3$)$_2$]$_2$, 5 g of benzene and 0.024 g (0.1 millimole) of triphenylphosphine, 18.68 g of triethoxysilane and 5.70 g of monoallylamine were added thereto and a reaction was then carried out at 150° C. for 3 hours, while stirring.

The product obtained was 2.10 g of γ-aminopropyltriethoxysilane, and the amount of the β-compound formed as the by-product was 0.098 g, which corresponded to 4.46% based on the aminopropyltriethoxysilane.

As apparent from the foregoing description, according to the process of the present invention, an aminopropylalkoxysilane can be obtained in a high yield from a hydrosilane compound and an allylamine compound while controlling the formation of the β-compound as the by-product below 1.5%, and the aminopropylalkoxysilane can be prepared at a low cost and a high efficiency.

We claim:

1. A process for the preparation of an aminopropylalkoxysilane, which comprises reacting a hydrosilane compound with an allylamine compound in the presence of at least one member selected from the group consisting of phosphorus compounds having a phosphorusnitrogen bond, which are represented by the following formulae:

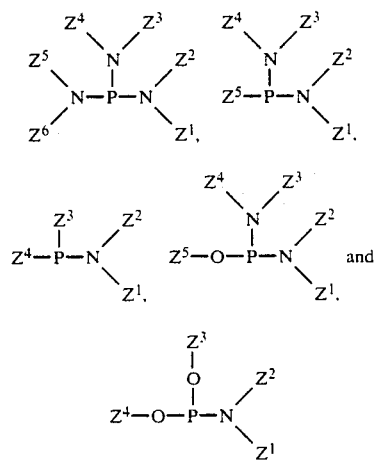

wherein Z$^1$, Z$^2$, Z$^3$, Z$^4$, Z$^5$, and Z$^6$ independently represent a hydrogen atom, an aliphatic hydrocarbon group having 1 to 8 carbon atoms, an alicyclic hydrocarbon group having 5 to 8 carbon atoms or an aromatic hydrocarbon group, and a rhodium compound.

2. A process according to claim 1, wherein the hydrosilane compound is selected from the compounds of the formula,

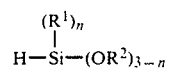

wherein R$^1$ represents a hydrogen atom, an aliphatic hydrocarbon group having 1 to 8 carbon atoms or an aromatic hydrocarbon group, R$^2$ represents a lower alkyl group, and n is 0, 1 or 2.

3. A process according to claim 2, wherein the hydrosilane compound is selected from trimethoxysilane, triethoxysilane, tripropoxysilane, triisopropoxysilane, tributoxysilane, triisobutoxysilane, methyldimethoxysilane, methyldiethoxysilane, methyldipropoxysilane, methyldibutoxysilane, ethyldimethoxysilane, ethyldiethoxysilane, vinyldimethoxysilane, vinyldiethoxysilane, phenyldimethoxysilane, phenyldiethoxysilane, dimethylmethoxysilane and dimethylethoxysilane.

4. A process according to claim 1, wherein the amine compound is selected from the compounds of the formula,

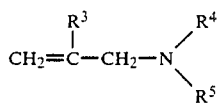

wherein $R^3$ represents a hydrogen atom or a lower alkyl group, and $R^4$ and $R^5$ independently represent a hydrogen atom, a lower alkyl group or a lower alkyl group substituted by a substituent containing at least one nitrogen atom.

5. A process according to claim 4, wherein the amine compound is selected from monoallylamine, diallylamine, triallylamine, methallylamine, N-methylallylamine, N,N-dimethylallylamine, N-ethylallylamine, N,N-diethylallylamine, N-allylaniline, N,N-methylallylaniline, allylethylenediamine, allyldiethylenetriamine and N,N-dimethyl-N'-allylethylenediamine.

6. A process according to claim 1, wherein the rhodium compound is selected from
$RhCl[P(C_6H_5)_3]_3$,
$[RhCl(CO)_2]_2$,
$RhCl(C_8H_{14})_2$,
$RhCl(t-BuNc)_4$,
$[RhCl(C_2H_4)]_2$,
$RhCl(CO)[P(C_6H_5)_3]_2$,
$Rh(OCOCH_3)_2]_2$,
$[Rh(OCOCF_3)_2]_2$,
$RhCl_3$, and
$Rh(CH_2COCH_2COCH_3)_3$.

7. A process according to claim 1, wherein the phosphorus compound is selected from
$P[N(CH_3)_2]_3$,
$P[N(C_2H_5)_2]_3$,
$P[N(n-C_3H_7)_2]_3$,
$P[N(iso-C_3H_7)_2]_3$,
$P[N(n-C_4H_9)_2]_3$,
$P[N(iso-C_4H_9)_2]_3$,
$P[N(t-C_4H_9)_2]_3$,
$P[N(CH_3)_2]_2[N(C_2H_5)_2]$,
$P[N(CH_3)_2][N(C_2H_5)_2]_2$,
$P[N(CH_3)(C_6H_5)]_3$,
$P[N(CH_3)(cyclo-C_6H_{11})]_3$,
$P[N(C_3H_5)_2]_3$,
$P[N(CH_3)_2]_2[N(CH_3)(C_6H_5)]$,
$P(C_6H_5)_2[N(n-C_4H_9)_2]$,
$P(C_2H_5)_2[N(CH_3)_2]$,
$P(C_6H_5)[N(n-C_4H_9)_2]_2$,
$P(n-C_4H_9)_2[N(n-C_4H_9)_2]$,
$P(OC_2H_5)_2[N(n-C_4H_9)_2]$,
$P(OCH_3)[N(CH_3)_2]_2$,
$P(OC_6H_5)_2[N(C_2H_5)_2]$, and
$P(C_6H_5)_2[N(CH_3)(C_6H_5)]$.

8. A process according to claim 1, wherein the reaction is carried out in the presence of hydrogen gas in addition to the phosphorus compound and the rhodium compound.

9. A process according to claim 8, wherein the hydrogen gas is present in an amount of 1/1000 to kg/cm².

10. A process according to claim 9, wherein the amount of the hydrogen gas is 1/10 to 3 kg/cm².

11. A process according to claim 1, wherein the reaction is carried out in the presence of a carboxylic acid in addition to the phosphorus compound and the rhodium compound.

12. A process according to claim 11, wherein the carboxylic acid is selected from benzoic acid, phthalic acid, isophthalic acid, terephthalic acid, maleic acid, phthalic anhydride, cyclohexane-carboxylic acid and acetic acid.

13. A process according to claim 1, wherein the catalyst consisting of the phosphorus compound and the rhodium compound is used in an amount of 1/10 to 1/100,000 mole per mole of the hydrosilane compound.

14. A process according to claim 13, wherein the amount of the catalyst is 1/50 to 1/20,000 mole per mole of the hydrosilane compound.

15. A process according to claim 1, wherein the phosphorus compound is used in an amount such that the molar ratio thereof to the rhodium metal of the rhodium compound is 1 to 20.

16. A process according to claim 1, wherein the amine compound is used in an amount such that the molar ratio thereof to the hydrosilane compound is 1/100 to 100.

17. A process according to claim 16, wherein the molar ratio is 1/10 to 10.

18. A process according to claim 1, wherein the reaction is carried out at a temperature of 0° to 200° C.

19. A process according to claim 18, wherein the reaction temperature is 30° to 170° C.

* * * * *

UNITED STATES PATENT AND TRADEMARK OFFICE
CERTIFICATE OF CORRECTION

PATENT NO. : 5,001,246

DATED : March 19, 1991

INVENTOR(S) : Yoshimasa Ishimura, Nobuyuki Nagato, Hideo Takahashi

It is certified that error appears in the above-identified patent and that said Letters Patent is hereby corrected as shown below:

Column 12, line 20, after "1/1000 to" insert --10--.

Signed and Sealed this

Twenty-ninth Day of September, 1992

Attest:

DOUGLAS B. COMER

*Attesting Officer*   *Acting Commissioner of Patents and Trademarks*